(12) United States Patent
Zhong

(10) Patent No.: US 12,301,971 B2
(45) Date of Patent: May 13, 2025

(54) PIPELINE ENDOSCOPE PROBE AND PIPELINE ENDOSCOPE ASSEMBLY

(71) Applicant: Qianhua Zhong, Yichun (CN)

(72) Inventor: Qianhua Zhong, Yichun (CN)

(73) Assignee: Shenzhen Andelian Technology Co., Ltd., Shenzhen (CN)

( * ) Notice: Subject to any disclaimer, the term of this patent is extended or adjusted under 35 U.S.C. 154(b) by 0 days.

(21) Appl. No.: 18/393,622

(22) Filed: Dec. 21, 2023

(65) Prior Publication Data

US 2024/0147044 A1    May 2, 2024

(51) Int. Cl.
| | |
|---|---|
| *H04N 23/50* | (2023.01) |
| *H04N 23/20* | (2023.01) |
| *H04N 23/55* | (2023.01) |
| *H04N 23/56* | (2023.01) |
| *H04N 23/65* | (2023.01) |

(52) U.S. Cl.
CPC ........... *H04N 23/555* (2023.01); *H04N 23/20* (2023.01); *H04N 23/55* (2023.01); *H04N 23/56* (2023.01); *H04N 23/65* (2023.01)

(58) Field of Classification Search
CPC ...... H04N 23/20; H04N 23/55; H04N 23/555; H04N 23/56; H04N 23/65; H04N 23/74
See application file for complete search history.

(56) References Cited

U.S. PATENT DOCUMENTS

| | | | |
|---|---|---|---|
| 2014/0333753 A1* | 11/2014 | Chapman | E03F 7/12 74/500.5 |
| 2020/0186683 A1* | 6/2020 | Warren | H04N 23/52 |

* cited by examiner

*Primary Examiner* — James M Pontius

(57) ABSTRACT

A pipeline endoscope probe includes a housing, an image capturing device and a lighting device. The housing defines a housing chamber and a through hole communicated with the housing chamber. The image capturing device is arranged in the accommodating chamber and the image capturing device is oriented towards the through hole. The image capturing device includes a lens and a first control board. The lens is configured to capture images, and the first control board is configured to receive the images captured by the lens and converts the images into image signals. The lighting device is arranged on the housing adjacent to the through hole, and a lighting direction of the lighting device matches orientation of the image capturing device.

19 Claims, 17 Drawing Sheets

PIPELINE ENDOSCOPE PROBE AND PIPELINE ENDOSCOPE ASSEMBLY

BACKGROUND OF THE INVENTION

The present disclosure relates to the technical field of pipeline endoscopes, in particular, to a pipeline endoscope probe and a pipeline endoscope assembly.

As a type of pipeline detection equipment, pipeline endoscopes can enable people to directly observe situation inside the pipeline without a need for disassembly or entry inside. It is helpful for maintenance, daily maintenance, and troubleshooting of pipelines. It can not only work in places with high temperature, toxicity, nuclear radiation, and cannot be directly observed by human eyes, but also be used for video detection of internal welds, corrosion, blockage, differences, foreign objects, and etc. in ventilation pipelines, air conditioning pipelines, water pipes, or industrial pipelines, greatly facilitating people's work and life.

At present, existing pipeline endoscope probes often rotate along with guide wires when being inserted into the pipeline. At this time, images observed by people will be flipped, causing inconvenience for users to observe the situation inside the pipeline. At the same time, due to the flipped images observed by people, it is difficult to determine a specific location of welds, corrosion, blockages, differences, foreign objects, etc. in the image, making it difficult for people to intuitively understand environment inside the pipeline and affecting their judgment. Moreover, due to darkness inside the pipeline, it is difficult to obtain clear images without external light sources.

SUMMARY OF THE INVENTION

In order to overcome above technological problems, the present disclosure provides a pipeline endoscope probe and a pipeline endoscope assembly.

An embodiment of the present disclosure provides a pipeline endoscope probe. The pipeline endoscope probe includes a housing, an image capturing device and a lighting device. The housing defines a housing chamber and a through hole communicated with the housing chamber. The image capturing device is arranged in the accommodating chamber and the image capturing device is oriented towards the through hole. The image capturing device includes a lens and a first control board. The lens is configured to capture images, and the first control board is configured to receive the images captured by the lens and converts the images into image signals. The lighting device is arranged on the housing adjacent to the through hole, and a lighting direction of the lighting device matches orientation of the image capturing device.

In at least one embodiment, the pipeline endoscope probe further includes an eccentric member. The eccentric member is rotatably arranged in the accommodating chamber, the image capturing device is fixedly connected to the eccentric member, and the image capturing device is coaxial with the eccentric member and rotates around an axis of the image capturing device under action of the eccentric member.

In at least one embodiment, the eccentric member defines an installation groove and a connecting block, at least a portion of the image capturing device is inserted into the installation groove to make the image capturing device coaxial with the eccentric member, and the connecting block is configured to be connected to a connecting piece passing through the image capturing device.

In at least one embodiment, the pipeline endoscope probe further includes an eccentric member housing and a bearing. The eccentric member housing is arranged in the accommodating chamber, the bearing is inserted into the eccentric member housing, and the eccentric member is rotatably inserted into a bearing hole of the bearing.

In at least one embodiment, the pipeline endoscope probe further includes a first fixing member, wherein the first fixing member is connected to one end of the eccentric member housing near the bearing, and the first fixing member is configured to fix the bearing inside the eccentric member housing.

In at least one embodiment, an inner wall of the eccentric member housing is provided with a limit protrusion resisting against the bearing to fix the bearing between the limit protrusion and the first fixing member.

In at least one embodiment, the lighting device includes multiple lamp beads, the housing is provided with lamp bead grooves around the through hole, and the lamp beads are arranged inside the lamp bead grooves.

In at least one embodiment, the pipeline endoscope probe further includes a lampshade connected to the housing and covers the lamp bead groove and the through hole.

In at least one embodiment, the pipeline endoscope probe further includes a second control board. The second control board is arranged in the accommodating chamber, and the second control board is electrically connected to the lighting device through a first electrical connection wire.

In at least one embodiment, an outer surface of the eccentric member housing is provided with a wiring groove, and the first electrical connection wire passes through the wiring groove.

In at least one embodiment, the pipeline endoscope probe further includes a second electrical connection wire. The eccentric member is provided with a wiring hole on one side thereof near the installation groove, and the second electrical connection wire passes through the wiring hole to achieve an electrical connection between the first control board and the second control board.

In at least one embodiment, the pipeline endoscope probe further includes a second fixing member. The second fixing member is connected to an inner wall of the accommodating chamber and resists against the second control board, so that the second control plate is limited between the first fixing member and the second fixing member.

In at least one embodiment, the pipeline endoscope probe further includes a connecting handle. The connecting handle includes a first connecting end and a second connecting end, the first connecting end is connected to one end of the housing away from the image capturing device, and the second connecting end is configured to be connected to a guide wire.

In at least one embodiment, an outer surface of the first connecting end is provided with an external thread, the accommodating chamber is provided with an internal thread at one end away from the image capturing device, and the external thread is threaded to the internal thread.

In at least one embodiment, the pipeline endoscope probe further includes a sealing ring, and an outer surface of the first connecting end is further provided with a sealing groove, the sealing ring is arranged in the sealing groove, and when the external thread is threaded to the internal thread, the sealing ring resists against between an inner wall of the accommodating chamber and an inner wall of the sealing groove.

In at least one embodiment, the connecting handle includes a spring arranged between the first connecting end and the second connecting end, and the spring is configured to deform under action of an inner wall of the pipeline.

In at least one embodiment, the pipeline endoscope probe further includes a third electrical connection wire. The second connection end is provided with an electrical connection part, and the third electrical connection wire passes through the first connection end and the spring to be electrically connected between the second control board and the electrical connection part, wherein the electrical connection part is electrically connected to the guide wire.

In at least one embodiment, the pipeline endoscope probe further includes a main control chip and a plurality of functional modules. The plurality of functional modules includes a power module, a storage module, a flash module, a switch control module, an infrared lighting module, an infrared control module, and the lens.

In at least one embodiment, the power module is configured to convert a first power supply voltage to a stabilized second power supply voltage, the second power supply voltage is configured to supply power to the storage module, the flash module, and the switch control module; a power pin, a clock signal pin, and a data pin of a storage control chip of the storage module are all electrically connected to the main control chip.

In at least one embodiment, a sampling pin, an input pin, an output pin, and a clock pin of a flash control chip of the flash module are all electrically connected to the main control chip.

In at least one embodiment, a signal transmission end and an image output end of the switch control module are connected to the main control chip, and the signal transmission end and the image output end are grounded through multiple switch branches, each of the switch branches includes a resistor and a control switch connected in series with the resistor.

In at least one embodiment, the infrared lighting module includes a transistor and a light-emitting element, a control end of the transistor is electrically connected to the main control chip, a first conductive end of the transistor is electrically connected to the power module, and a second conductive end of the transistor is grounded through the light-emitting element.

In at least one embodiment, the infrared control module includes an infrared filtering control chip, which is an IR-CUT dual filter control chip configured to control operation of infrared dual filter plates in the lens.

Another embodiment of the present disclosure provides a pipeline endoscope assembly. The pipeline endoscope assembly includes a display and the pipeline endoscope probe. The pipeline endoscope probe is configured to be in a communication connection with the display and to transmit image signals to the display.

The beneficial effect of the present disclosure is that, by such arrangements, the lens can capture images, and an imaging element on the first control board converts the images into signals, which can be effectively transmitted; the lighting device can provide illumination, making the images captured by the image capturing device clearer, allowing users to better understand the situation inside the pipeline and more convenient to use. Moreover, the lighting direction of the lighting device matches the orientation of the image capturing device, effectively illuminating the environment in front of the image capturing device, improving efficiency and clarity of image capturing by the image capturing device.

BRIEF DESCRIPTION OF DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION OF THE INVENTION

Figure 1:
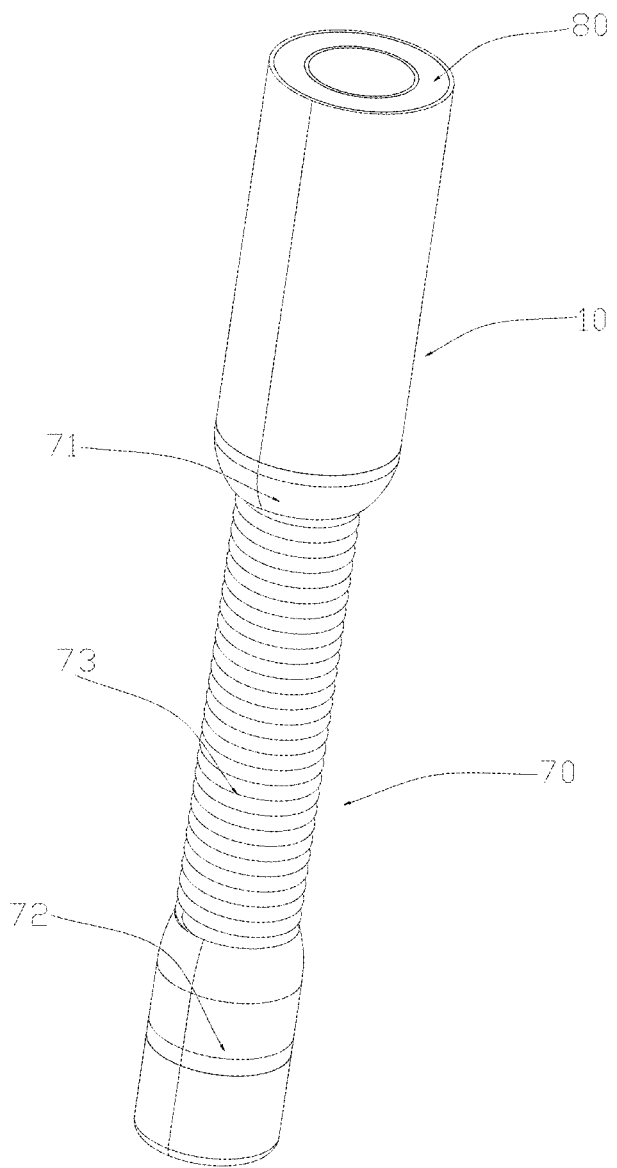
FIG. 1 is a schematic structural diagram of a pipeline endoscope probe taken from a first view according to a first embodiment of the present disclosure.
Figure 2:
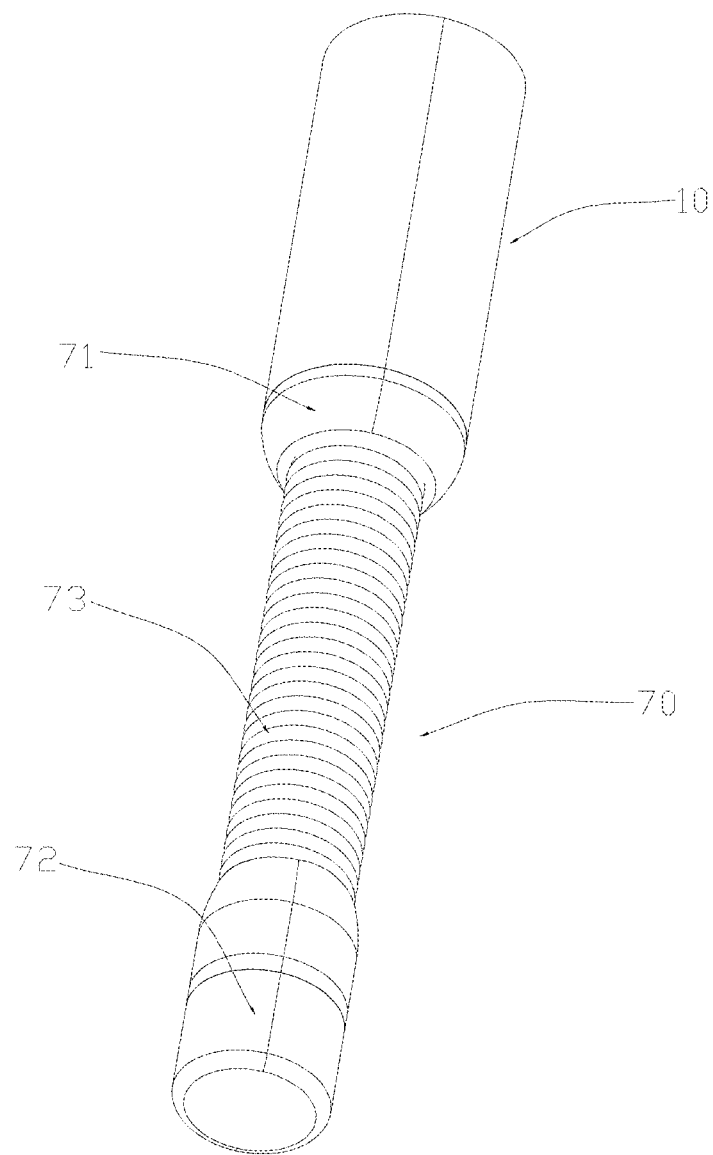
FIG. 2 is a schematic structural diagram of the pipeline endoscope probe of FIG. 1 taken from a second view.
Figure 3:
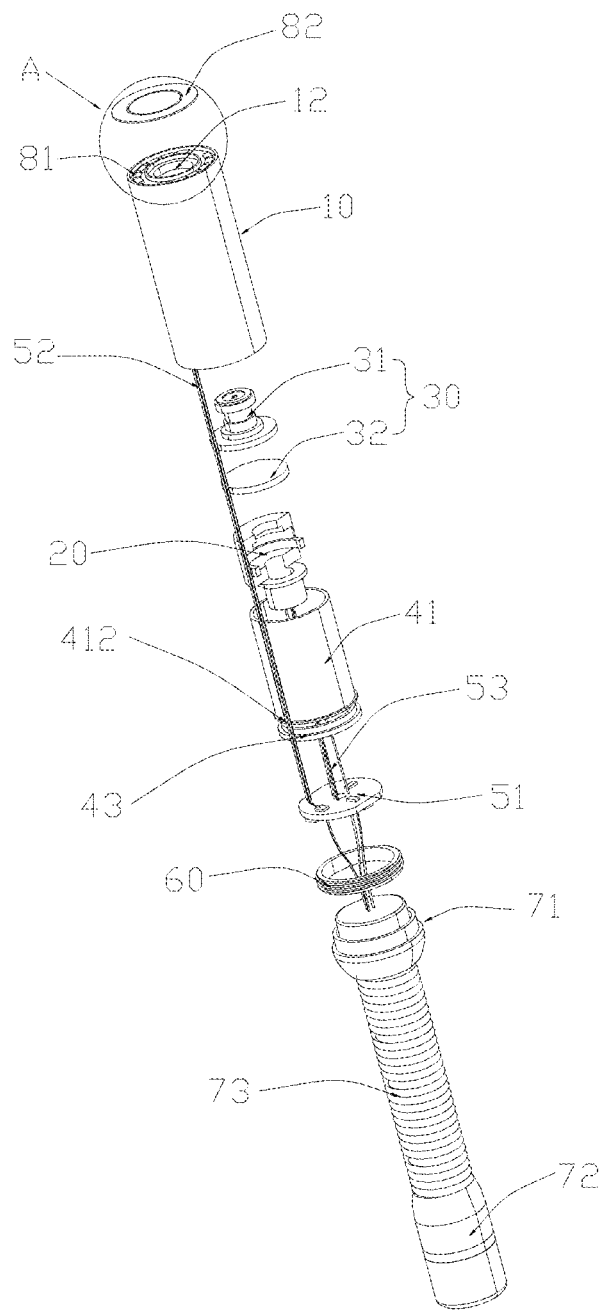
FIG. 3 is an exploded view of the pipeline endoscope probe of FIG. 1 taken from a first view.
Figure 4:
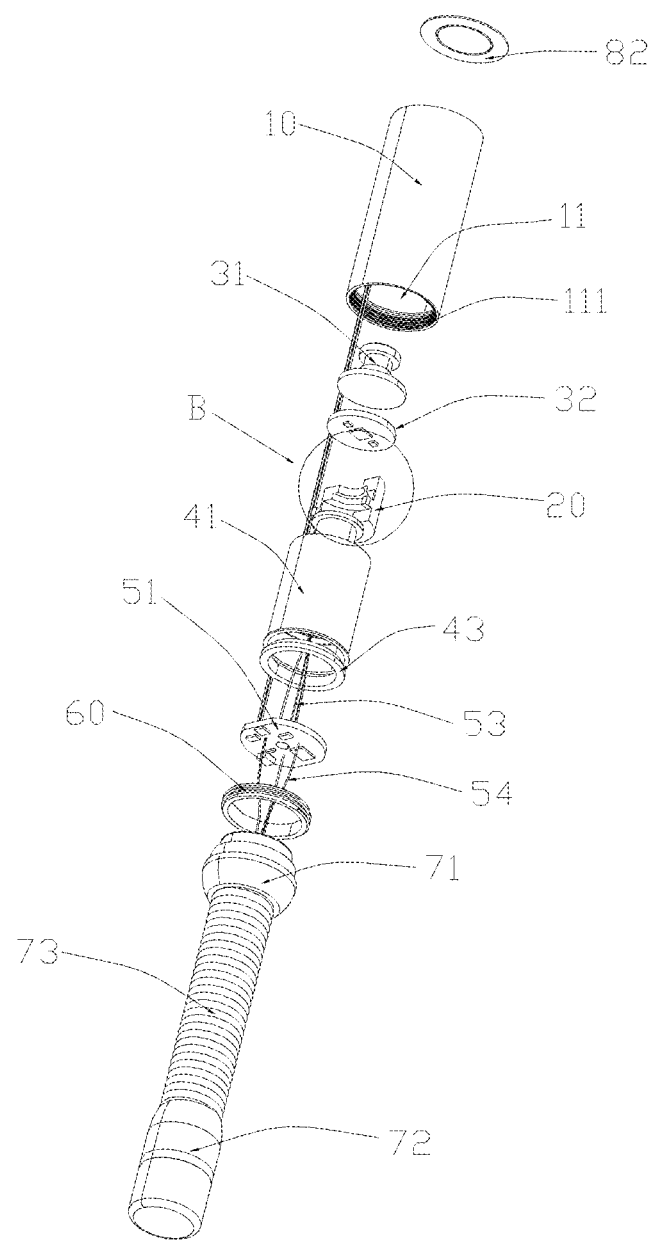
FIG. 4 is an exploded view of the pipeline endoscope probe of FIG. 1 taken from a second view.
Figure 5:
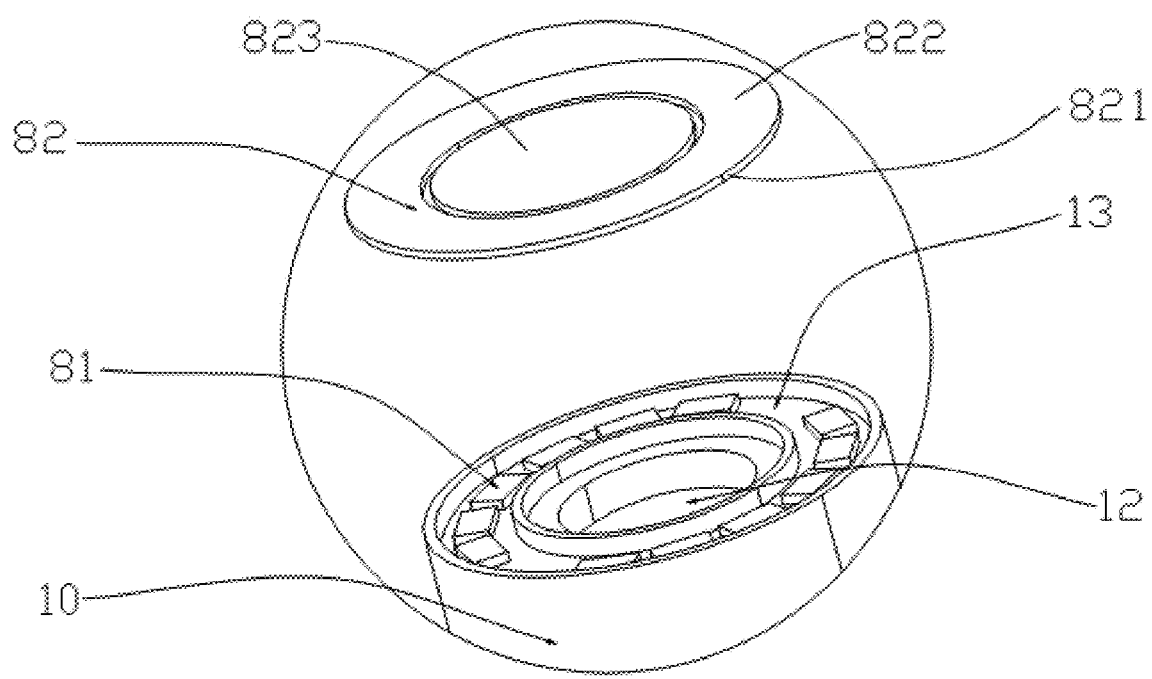
FIG. 5 is an enlarged view of the portion A shown in FIG. 3.
Figure 6:
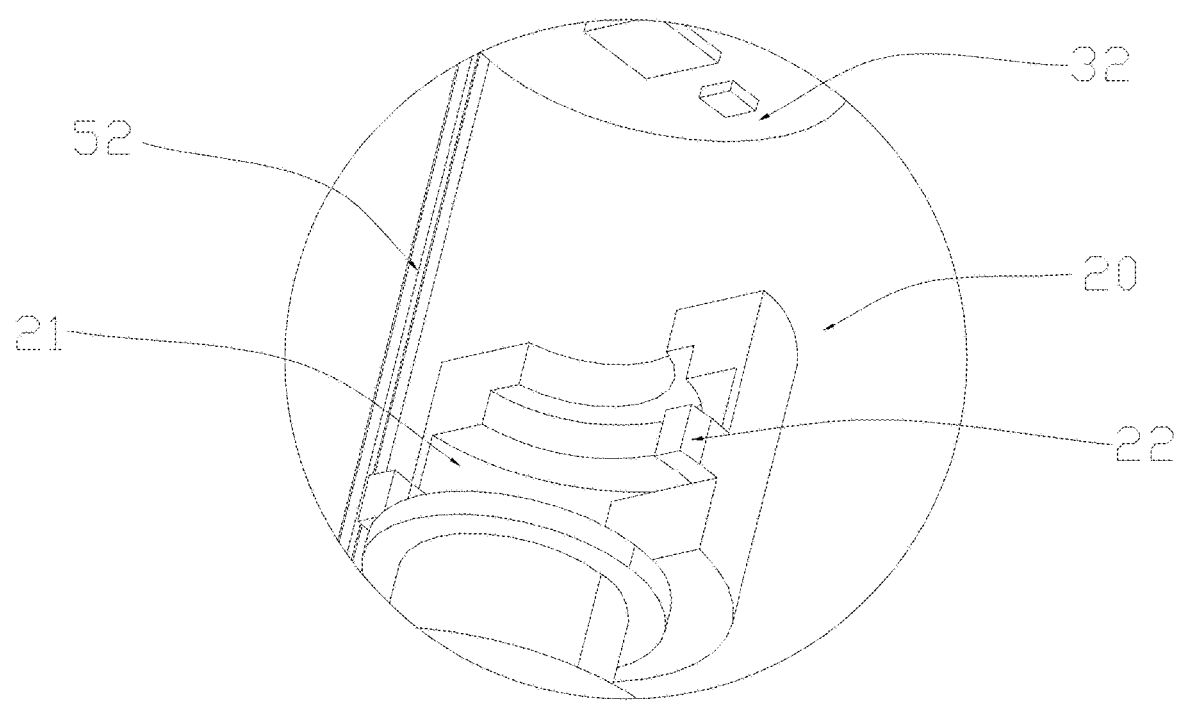
FIG. 6 is an enlarged view of the portion B shown in FIG. 4.
Figure 7:
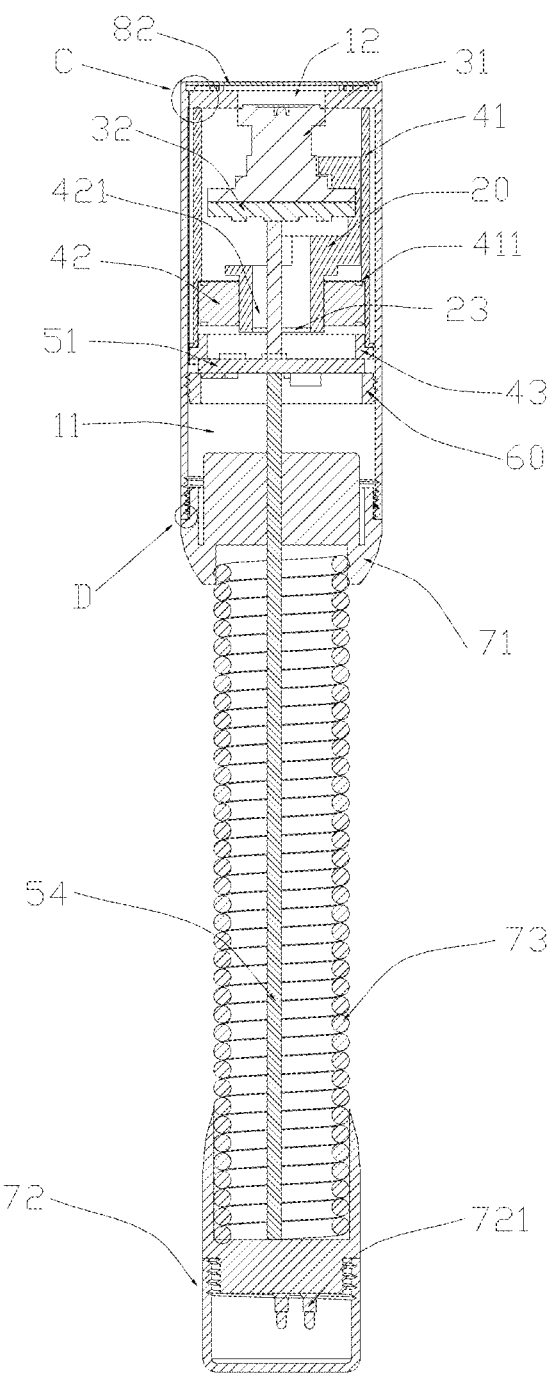
FIG. 7 is a sectional view of the pipeline endoscope probe of FIG. 1.
Figure 8:
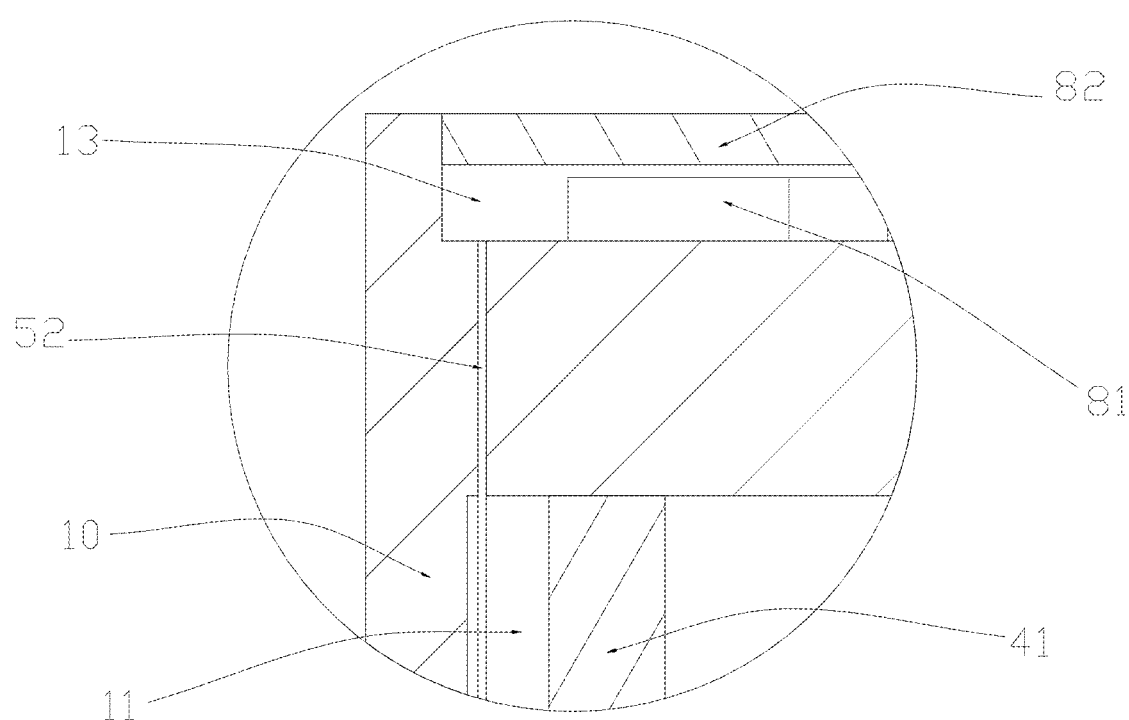
FIG. 8 is an enlarged view of the portion C shown in FIG. 7.
Figure 9:
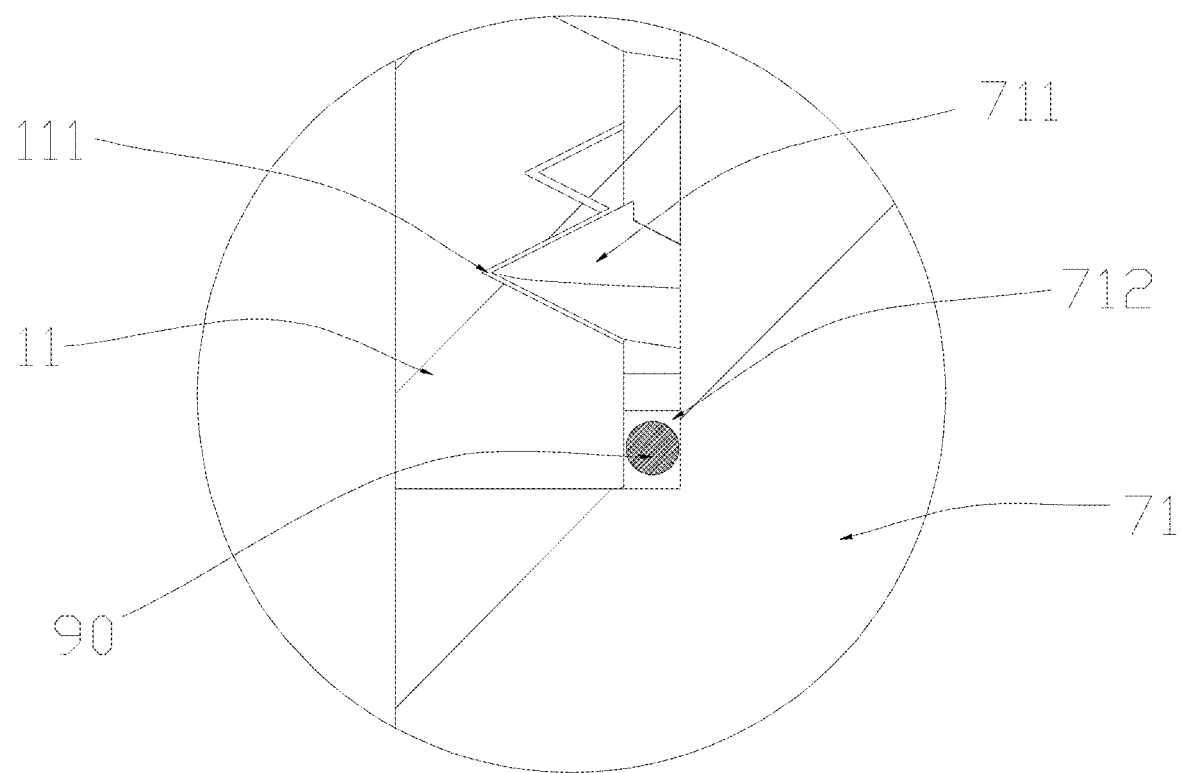
FIG. 9 is an enlarged view of the portion D shown in FIG. 7.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "comprising" when utilized, means "including, but not necessarily limited to"; it specifically indicates open-ended inclusion or membership in the so-described combination, group, series, and the like. The disclosure is illustrated by way of example and not by way of limitation in the figures of the accompanying drawings in which like references indicate similar elements. It should be noted that references to "an" or "one" embodiment in this disclosure are not necessarily to the same embodiment, and such references can mean "at least one". In addition, the terms "first" and "second" are used for descriptive purposes only and cannot be understood as indicating or implying relative importance or implying the number of indicated technical features. Thus, the features defined as "first" and "second" may explicitly or implicitly include one or more of the said features. In the description of embodiments of the application, "a plurality of" means two or more, unless otherwise specifically defined.

It should be noted that when a component is described as to be "fixed" on another component, it may be directly on said another component or may be fixed to said another component through an intermediate component. When one component is considered to be "connected" to another component, it may be connected directly to another component or may be connected to another component via an intermediate component. The terms "inside", "outside", "left", "right" and the like used herein are for purposes of illustration only and are not intended to represent the only embodiment.

Unless otherwise defined, all technical and scientific terms used in the present disclosure have the same meaning as those commonly understood by those skilled in the art. The terms used in the present disclosure are merely intended to describe specific embodiments, and are not intended to limit this application. The term "and/or" as used herein includes any and all combinations of one or more associated listed items.

Referring to FIGS. 1-9, an embodiment of the present disclosure provides a pipeline endoscope probe, which includes: a housing 10 and an image capturing device 30. The housing 10 defines an accommodating chamber 11 and a through hole 12 communicated with the accommodating chamber 11. The image capturing device 30 is rotatably arranged inside the accommodating chamber 11 and is oriented towards the through hole 12. The image capturing device 30 includes a lens 31 configured to capture images and a first control board 32 configured to receive the images captured by the lens 31 and to convert them into image signals.

The housing 10 is equipped with a lighting device 80 adjacent to the through hole 12, and the illumination direction of the lighting device 80 matches the orientation of the image capturing device 30.

By such arrangements, the lens 31 can capture images, and an imaging element on the first control board 32 converts the images into signals, which can be effectively transmitted; the lighting device 80 can provide illumination, making the images captured by the image capturing device 30 clearer, allowing users to better understand the situation inside the pipeline and more convenient to use. Moreover, the lighting direction of the lighting device 80 matches the orientation of the image capturing device 30, effectively illuminating the environment in front of the image capturing device 30, improving efficiency and clarity of image capturing by the image capturing device 30; in addition, the image capturing device 30 can rotate within the accommodating chamber 11, facilitating users to change their perspective to obtain a clearer and more intuitive view of the situation inside the pipeline.

In the embodiment, the pipeline endoscope probe further includes an eccentric member 20, which can be rotatably arranged in the accommodating chamber 11. The image capturing device 30 is fixedly connected to the eccentric member 20 and is coaxially arranged with the eccentric member 20 and rotates around an axis of the image capturing device 30 under action of the eccentric member 20. By such arrangement, when in use, the pipeline endoscope probe is inserted into the pipeline, and the eccentric member 20 rotates under action of gravity, thereby driving the image capturing device to rotate to ensure the perspective of the lens of the image capturing device is always upright, preventing the image capturing device from rotating along with the pipeline endoscope probe when the pipeline endoscope probe is inserted into the pipeline, and maintaining stability of the images captured by the image capturing device, thus facilitating users to better understand the situation inside the pipeline based on the images captured by the image capturing device.

In the embodiment, the eccentric member 20 is provided with an installation groove 21 and a connecting block 22. At least a portion of the image capturing device 30 is inserted into the installation groove 21 to have the image capturing device 30 coaxially arranged with the eccentric member 20. The connecting block 22 is configured to be connected to a connecting piece passing through the image capturing device 30. By such arrangement, the image capturing device 30 can be inserted into the installation groove 21, which can make the image capturing device more stably connected to the eccentric member 20 on one hand, and can also make the image capturing device 30 coaxial with the eccentric member 20 on the other hand. Rotation of the image capturing device 30 along with the eccentric member 20 becomes smoother. Through the connection block 22, the image capturing device 30 can be further stably connected to the eccentric member 20, which prevents the image capturing device 30 from detaching from the installation groove 21 to improve stability of the pipeline endoscope probe.

In the embodiment, the pipeline endoscope probe further includes an eccentric member housing 41 and a bearing 42. The eccentric member housing 41 is arranged in the accommodating chamber 11, the bearing 42 is inserted into the eccentric member housing 41, and the eccentric member 20 is rotatably inserted into a bearing hole 421 of the bearing 42. By such arrangement, the bearing 42 can make rotation of the eccentric member 20 around the rotation axis more smoothly, thereby driving the image capturing device 30 to rotate synchronously, making the pipeline endoscope probe more flexible. When the pipeline endoscope probe is flipped, under the action of gravity, the image capturing device 30 can rotate quickly and flexibly to ensure the images captured by the image capturing device 30 to keep upright, which is convenient for users to view the situation inside the pipeline based on the images captured by the image capturing device 30. The eccentric member housing 41 can better protect the image capturing device 30 and the eccentric member 20, and the eccentric member housing 41, image capturing device 30, and the eccentric member 20 are formed an integrated structure, which is also convenient for assembly and improves manufacturing efficiency.

In the embodiment, the pipeline endoscope probe further includes a first fixing member 43 connected to one end of the eccentric member housing 41 adjacent to the bearing 42. The first fixing member 43 is configured to fix the bearing 42 inside the eccentric member housing 41. By such arrangement, the first fixing member 43 can fix the bearing 42, which prevents the eccentric member 20 and the image capturing device 30 from detaching from the eccentric member housing 41, and improve the stability of the pipeline endoscope probe.

In the embodiment, an inner wall of the eccentric member housing 41 is equipped with a limit protrusion 411, which resists against the bearing 42 to fix the bearing 42 between the limit protrusion 411 and the first fixing member 43. By such arrangement, two opposite ends of the bearing 42 are respectively resists against the limit protrusion 411 and the first fixing member 43, which can further fix the bearing 42, limit its axial movement, thus improving the stability of the pipeline endoscope probe.

In the embodiment, the lighting device 80 includes a plurality of lamp beads 81. The housing 10 is provided with lamp bead grooves 13 around the through hole 12. The plurality of lamp beads 81 are arranged inside the lamp bead grooves 13 respectively. The lamp beads 81 are arranged inside lamp bead grooves 13 and surrounds the through hole 12, which can make light around through hole 12 more uniform, thereby making the light in the environment in front of image capturing device 30 more uniform. The image capturing device 30 captures clearer images, preventing definition of the image from being affected due to too dark or too bright local light.

In the embodiment, the lighting device 80 further includes a lampshade 82, which is connected to the housing 10 and covers the lamp bead grooves 13 and the through hole 12. The lampshade 82 can effectively isolate the lamp beads 81 and image capturing device 30 from external environment, improve sealing of the pipeline endoscope probe, protect the lamp beads 81 and image capturing device 30 from being damaged by debris in the pipeline, and improve the service life of the pipeline endoscope probe. Preferably, the lampshade 82 is made of transparent high-strength glass, plastic, or resin, and etc. In particular, the lampshade 82 is a planar plate having a first flat surface 821, an opposite second flat surface 822 and a central through hole 823 running through the first flat surface 821 and the second flat surface 822, the central through hole 823 surrounds the through hole 12, the first flat surface 821 is inserted in the lamp bead groove 13 and faces the multiple lamp beads 81, and the second flat surface 822 faces outside and is flush with an end of the lamp bead groove 13.

In the embodiment, the pipeline endoscope probe further includes a second control board 51 arranged in the accommodating chamber 11. The second control board 51 is electrically connected to the lighting device 80 through a first electrical connection wire 52. The second control board 51 can control the lighting device 80 according to user instructions, such as turning on or off part of the lamp beads 81, or adjusting a brightness of light beads 81. When the light in the pipeline is insufficient, the lighting device 80 can provide compensating light; and when the light in the pipeline is sufficient, at least part of the lamp beads 81 can be turned off to save electricity. At the same time, adjusting the light intensity can change the brightness of the environment, prevent the images captured by the image capturing device 30 from overexposure due to excessive brightness, ensure the definition of the images captured by the image capturing device 30, and help users more clearly understand the situation inside the pipeline.

In the embodiment, an outer surface of the eccentric member housing 41 is provided with a wiring groove 412. The first electrical connection wire 52 passes through the wiring groove 412 and is accommodated between the wiring groove 412 and the inner wall of the housing 10. By such arrangement, the wiring groove 412 can effectively store the first electrical connection wire 52, which ensures stability of an electrical connection between the second control board 51 and the lighting device 80. At the same time, it can effectively prevent the first electrical connection wire 52 from obstructing insertion of the eccentric member housing 41 when the eccentric member housing 41 is inserted into the accommodating chamber 11, thereby improving efficiency of assembly and manufacture of the pipeline endoscope probe.

In the embodiment, the pipeline endoscope probe further includes a second electrical connection wire 53. The eccentric member 20 defines a wiring hole 23 on one side thereof near the installation groove 21. The second electrical connection wire 53 passes through the wiring hole 23 to achieve an electrical connection between the first control board 32 and the second control board 51. By such arrangement, the second electrical connection wire 53 passes through the wiring hole 23, which can achieve the electrical connection between the first control board 32 and the second control board 51, and prevent the rotation of the eccentric member 20 from being affected by the second electrical connection wire 53, thus further improving the stability of the pipeline endoscope probe.

In the embodiment, the pipeline endoscope probe further includes a second fixing member 60. The second fixing member 60 is connected to an inner wall of the accommodating chamber 11 and resists against the second control board 51, so that the second control board 51 is limited between the first fixing member 43 and the second fixing member 60. By such arrangement, the second fixing member 60 and the first fixing member 43 fix the second control board 51, which further improves the stability of the pipeline endoscope probe and prevents the second control board 51 from moving inside the accommodating chamber 11. Preferably, the second fixing member 60 is connected to the inner wall of the accommodating chamber 11 through a threaded portion, which enhances the stability of the connection.

In the embodiment, the pipeline endoscope probe further includes a connecting handle 70. The connecting handle 70 includes a first connecting end 71 and a second connecting end 72. The first connecting end 71 is connected to one end of the housing 10 away from the image capturing device 30, and the second connecting end 72 is configured to be connected to guide wires. The first connecting end 71 is connected to one end of the housing 10 away from the image capturing device 30, which can cover the accommodating chamber 11 to form a closed space to protect the image capturing device 30, the first control board 32, and the second control board 51 inside the accommodating chamber 11, thus preventing these components from being stained by debris in the pipeline, and improving the stability of the pipeline endoscope probe. The second connecting end 72 is connected to the guide wires, which can achieve transmission of image signals. When the connecting wire is inserted into the pipeline, the pipeline endoscope probe can go deeper into the pipeline along with the guide wires, which makes it convenient for users to use.

In the embodiment, an outer surface of the first connecting end 71 is provided with an external thread 711, and the accommodating chamber 11 is provided with an internal thread 111 at one end away from the image capturing device 30. The external thread 711 is threaded to the internal thread 111. By such arrangement, combination of the internal thread 111 and the external thread 711 can effectively improve stability of the connection between the first connecting end 71 and the housing 10, prevent detachment of the first connecting end 71 from the housing 10 when the pipeline endoscope probe goes deep into the pipeline, and effectively protect the safety of user's property.

In the embodiment, the pipeline endoscope probe further includes a sealing ring 90, and the outer surface of the first connecting end 71 is further provided with a sealing groove 712. The sealing ring 90 is arranged inside the sealing groove 712. When the external thread 711 is threaded to the internal thread 111, the sealing ring 90 is clamped between an inner wall of the accommodating chamber 11 and an inner wall of the sealing groove 712. By such arrangement, the sealing ring 90 can be abutted against the inner wall of the accommodating chamber 11 and the inner wall of the sealing groove 712, which can further enhance sealing between the housing 10 and the first connecting end 71, thus preventing the components inside the accommodating chamber from being stained by debris in the pipeline.

In the embodiment, the connecting handle 70 further includes a spring 73 arranged between the first connecting end 71 and the second connecting end 72. The spring 73 is configured to deform under action of the inner wall of the pipeline. Such arrangement can improve adaptability of the pipeline endoscope probe. The pipeline endoscope probe can be inserted into the pipeline during use even if the environment inside the pipeline is complicated when in use. The housing is cylindrical in shape, with an outer diameter of 20 mm-25 mm and a length of 55 mm-60 mm. The housing with such size can adapt to sewers with larger inner diameter. At the same time, a length of the spring is 60 mm-63 mm and a diameter of the spring is 12 mm-17 mm. The housing with a longer length is benefit for improving stability of the lens inside the housing, and can maintain the stability of the lens inside the housing, which is adapted to wider and straighter pipelines. The spring has a shorter length, making it less likely to shake when the pipeline endoscope probe enters the pipeline along with the guide wires, which ensures stability of the images captured by the image capturing device to obtain a clearer view of the situation inside the pipeline, thus effectively improving user experience. The second connecting end has a length of 28 mm-32 mm, which facilitates connection to the guide wires and extension into the pipeline together with the spring.

In the embodiment, the pipeline endoscope probe further includes a third electrical connection wire 54. The second connection end 72 is equipped with an electrical connection part 721. The third electrical connection wire 54 passes through the first connection end 71 and the spring 73, and is electrically connected between the second control board 51 and the electrical connection part 721. The electrical connection part 721 is configured to be electrically connected to the guide wires. The third electrical connection wire 54 passes through the first connection end 71 and the spring 73, ensuring stability of the electrical connection. The spring 73 and the first connection end 71 can provide protection for the third electrical connection wire 54, ensuring stability of the pipeline endoscope probe.

Figure 10:
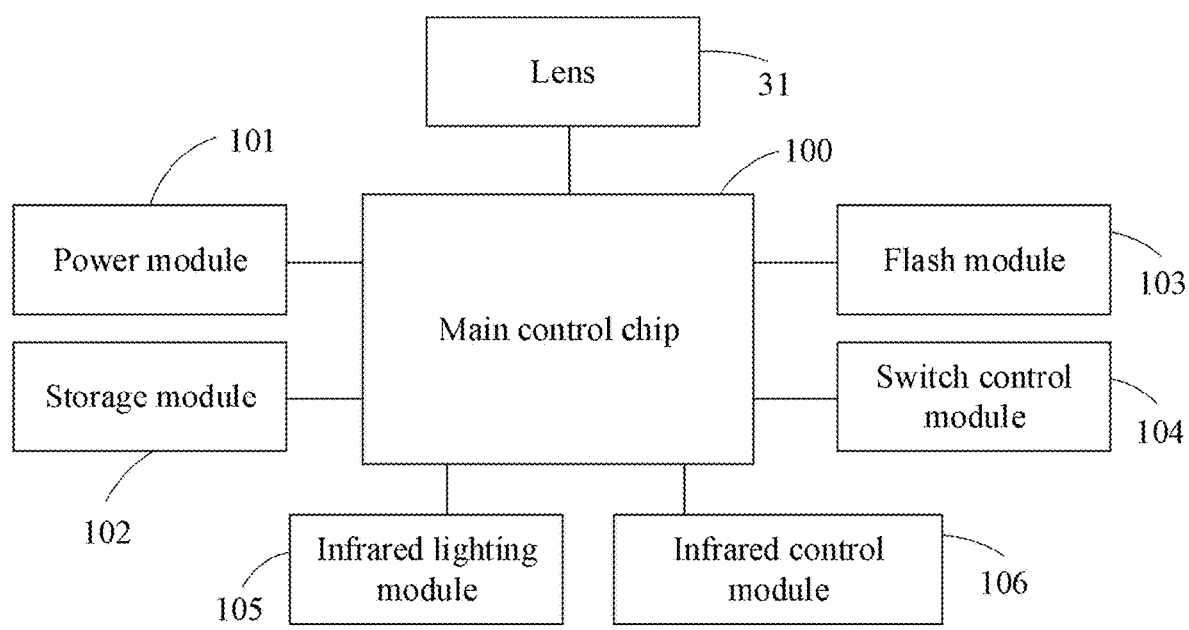
FIG. 10 is a schematic diagram of the circuit block of the pipeline endoscope probe of FIG. 1.

In the pipeline endoscope probe, the first control board 32 and the second control board 51 constitute a control module of the pipeline endoscope probe configured to communicate with an external device (such as, the display 15) to transmit the image signals to the external device. Referring to FIG. 10, the control module may include a main control chip 100 and a plurality of functional modules electrically connected to the main control chip respectively. The plurality of functional modules may include a power module 101, a storage module 102, a flash module 103, a switch control module 104, an infrared lighting module 105, an infrared control module 106 and the lens 31.

Specifically, the main control chip 100 and the plurality of functional modules can be arranged on the first control board 32 or the second control board 51 according to actual needs. In addition, in other embodiments, the first control board 32 and the second control board 51 can be integrated into one piece and the main control chip 100 and the plurality of functional modules are arranged on the one piece. In the embodiment, the storage module 102 is arranged on the first control board 32 and other functional modules are arranged on the second control board 51.

Figure 11:
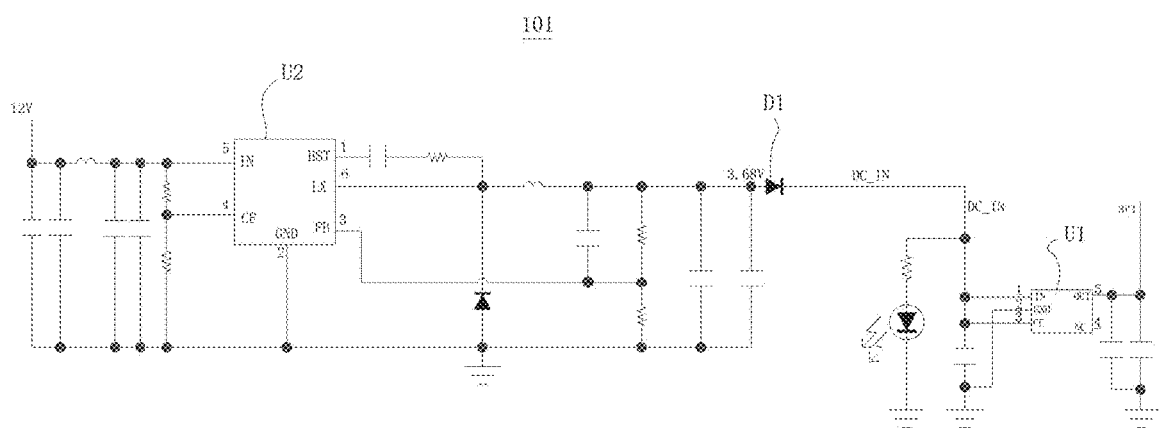
FIG. 11 is the circuit diagram of a power module of the pipeline endoscope probe shown in FIG. 10.

Referring to FIG. 11, the power module 101 includes a main power supply chip U2, a regulator chip U1, a power supply signal input end 1011 and a power supply signal output end 1012. The power supply signal input end 1011 is configured to receive a first power supply voltage (such as a direct voltage of 12 voltages), the main power supply chip U2 is configured to covert the first power supply voltage into a converted voltage (such as a direct voltage of 3.68V). The converted voltage is processed to be a stable second power supply voltage (such as a direct voltage of 3.3V) by the diode D1 and the regulator chip U3. The second power supply voltage is configured to supply power to the storage module 102, the flash module 103, the switch control module 104, and etc.

Figure 12:
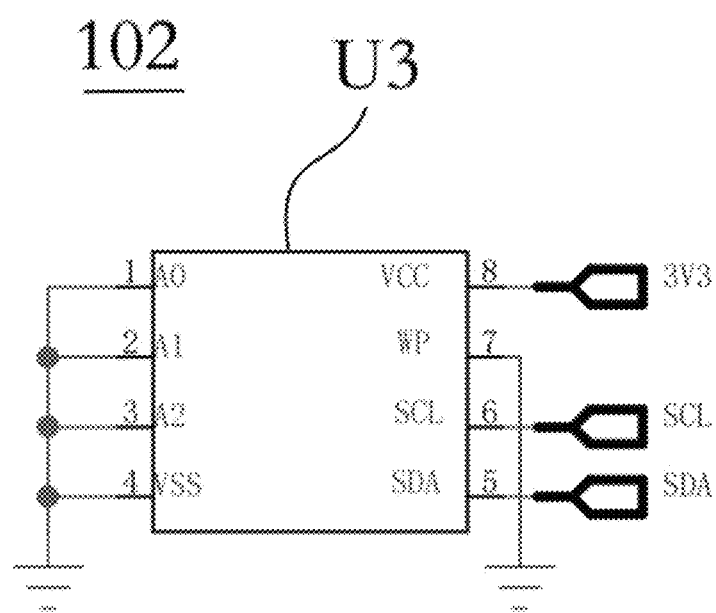
FIG. 12 is a circuit diagram of a storage module of the pipeline endoscope probe shown in FIG. 10.

Referring to FIG. 12, a power pin VCC, a clock signal pin SCL, and a data pin SDA of a storage control chip U3 of the storage module 102 are all electrically connected to the main control chip 100. The storage module 102 is configured to temporarily store images collected by the lens 31.

Figure 13:
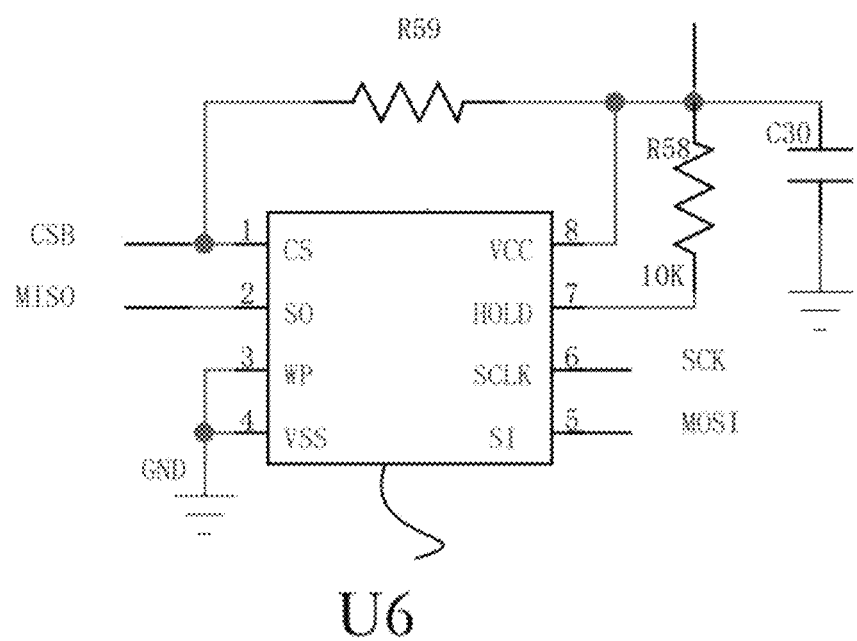
FIG. 13 is a circuit diagram of a flash module of the pipeline endoscope probe shown in FIG. 10.

Referring to FIG. 13, a sampling pin CSB, an input pin MIS0, an output pin MOS1, and a clock pin of a flash control chip U6 of the flash module 103 are all electrically connected to the main control chip 100.

Figure 14:
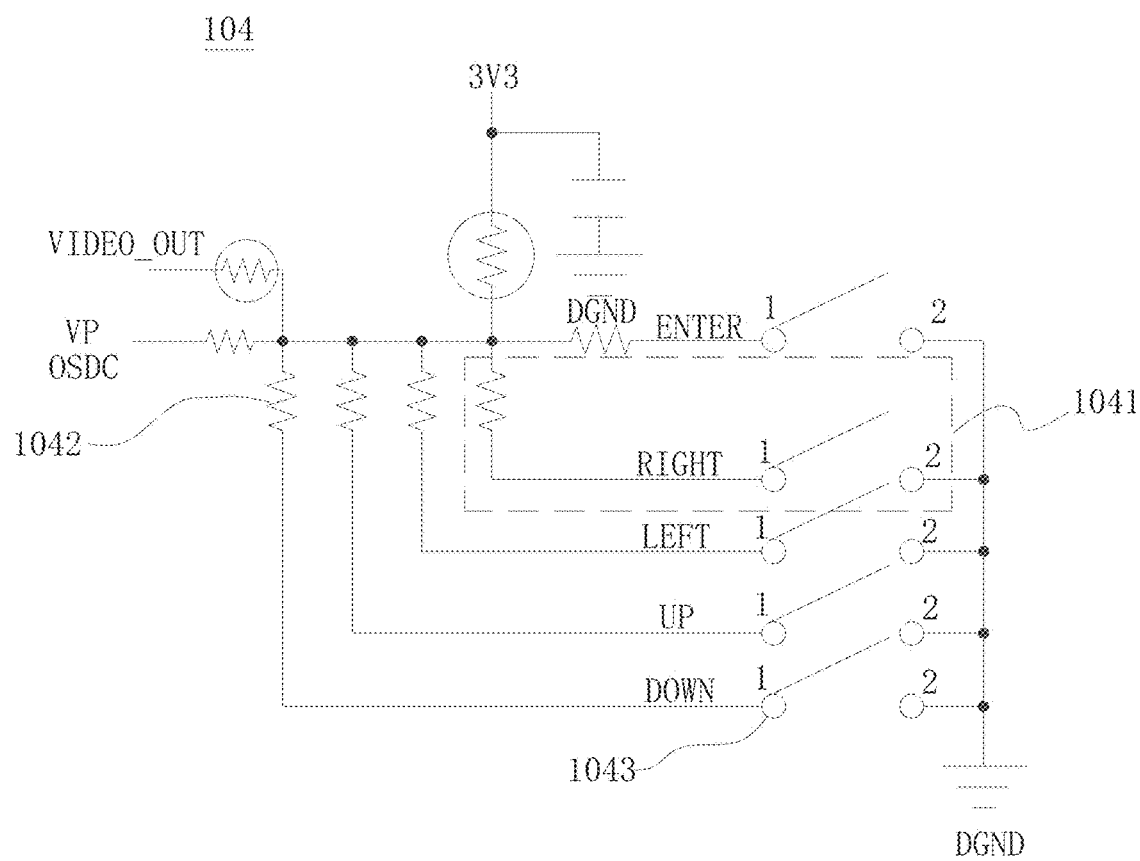
FIG. 14 is a circuit diagram of a switch control module of the pipeline endoscope probe shown in FIG. 10.

Referring to FIG. 14, a signal transmission end VP and an image output end VODEO OUT of the switch control module 104 are connected to the main control chip 100, and the signal transmission end VP and the image output end VODEO OUT are grounded through multiple switch branches 1041. Each of the switch branches 1041 includes a resistor 1042 and a control switch 1043 connected in series with the resistor 1042. Each switch branch 1041 is configured to control on/off of switches, lighting, and other functions based on instructions generated by user operation.

Figure 15:
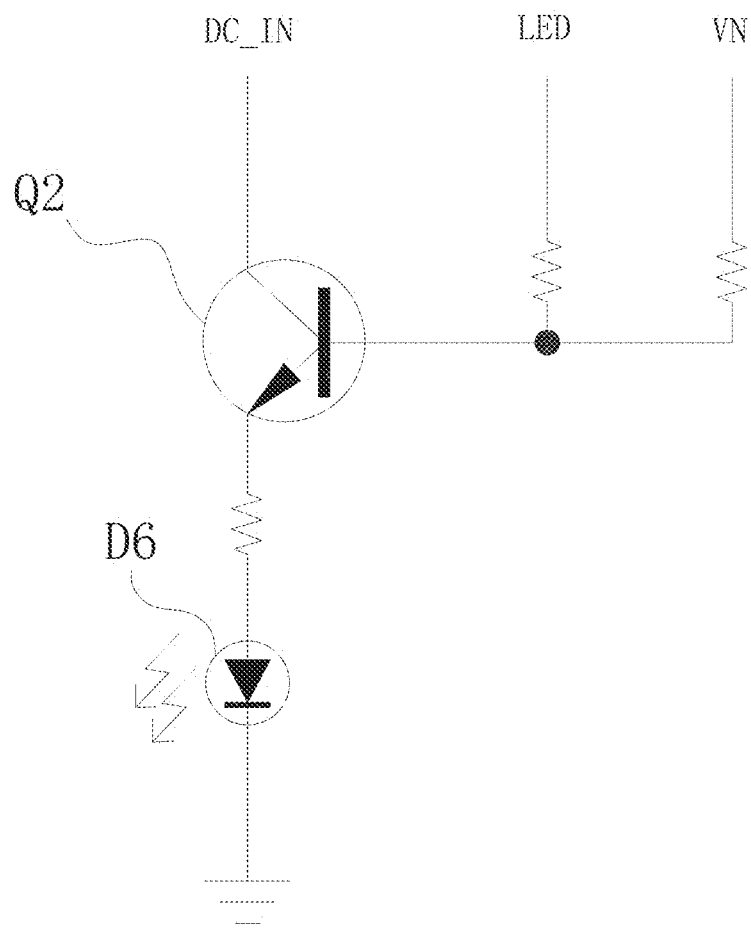
FIG. 15 is a circuit diagram of the infrared lighting module of the pipeline endoscope probe shown in FIG. 10.

Referring to FIG. 15, the infrared lighting module 105 includes a transistor Q2 and a light-emitting element D6. A control end of the transistor Q2 is electrically connected to the main control chip 100, and a first conductive end of the transistor Q2 is electrically connected to the power module 101. A second conductive end of the transistor Q2 is grounded through the light-emitting element D6. The light-emitting element D6 can be turned on under the control of the main control chip 100 to emit infrared light, enabling the lens 31 to achieve image capturing in a dark environment.

Figure 16:
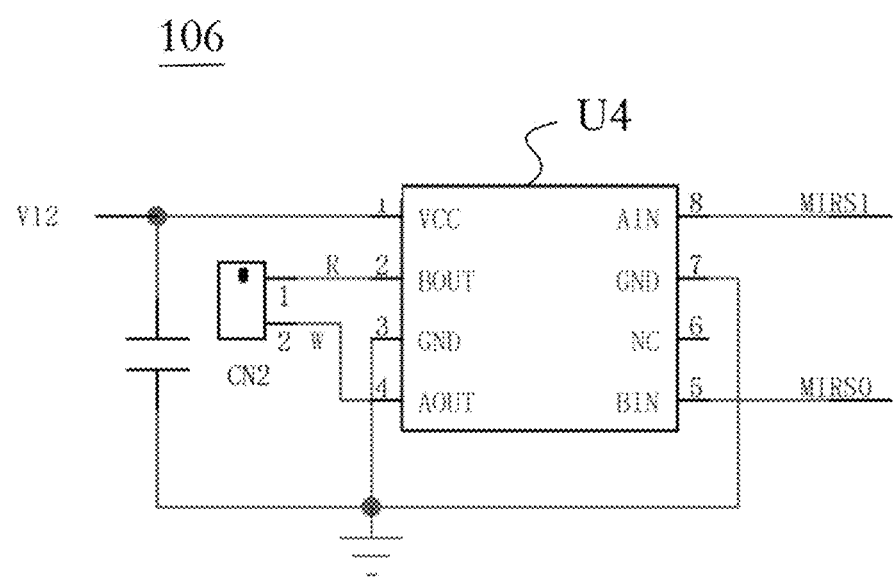
FIG. 16 is a circuit diagram of an infrared control module of the pipeline endoscope probe shown in FIG. 10.

Referring to FIG. 16, the infrared control module 106 includes an infrared filtering control chip U4, which is an IR-CUT dual filter control chip configured to control operation of infrared dual filter plates in the lens 31. Specifically, the infrared filtering control chip U4 is configured to control the infrared dual filter plates in the lens 31 to automatically switch filters when an infrared sensor arranged on an outside of the lens 31 detects a change of light intensity, so as to achieve a better imaging effect. That is, the infrared dual filters plates in the lens 31 can automatically switch filters either in day or night, so the lens 31 can achieve best imaging effect regardless of whether it is during the day or night.

Figure 17:
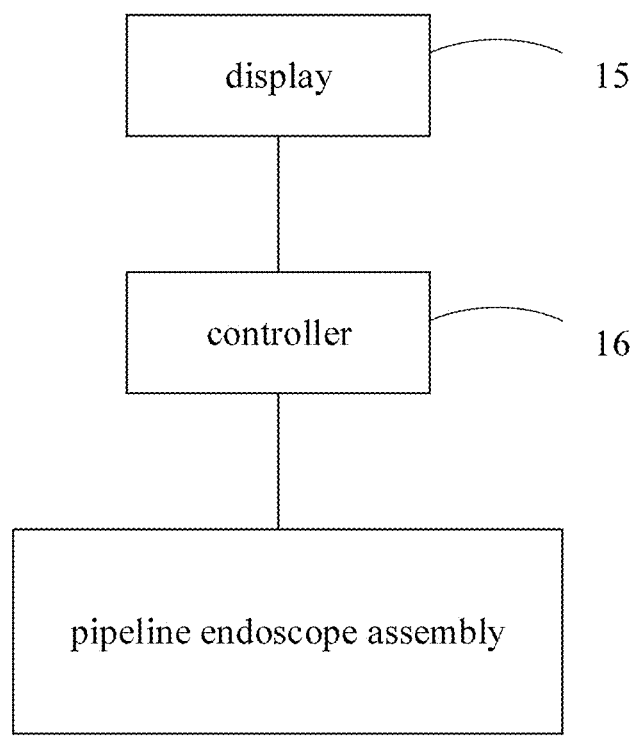
FIG. 17 is a block diagram of the pipeline endoscope assembly according to an embodiment of the present disclosure.

As shown in FIG. 17, a pipeline endoscope assembly provided in an embodiment of the present disclosure includes a display 15 and a pipeline endoscope probe as shown in FIGS. 1 to 9. The pipeline endoscope probe is in a communication connection with the display 15 and configured to transmit the image signals to the display 15. Specifically, the pipeline endoscope probe can be electrically connected to the display 15 through a bendable electrical connection cable, with its length generally set according to actual needs. The image signals collected by the pipeline endoscope probe is transmitted to the display 15 through the controller 16 for image display. Specifically, due to presence of the eccentric member 20, The pipeline endoscope probe can maintain an upright direction to capture the images, and the display 15 can maintain an upright direction based on the images. It can be understood that the upright direction is a direction that facilitates users to observe, such as a direction contrary to the gravity.

The technical features in the foregoing embodiments may be combined in any manner. To make the description brief, all possible combinations of the technical features in the foregoing embodiments are not described. However, as long as there is no contradiction between the combinations of the technical features, it should be considered as the scope described in this specification. The foregoing embodiments represent only several embodiments of the present disclosure, and descriptions thereof are relatively specific and detailed, but may not be construed as a limitation on the scope of the present disclosure. It should be noted that an ordinary person skilled in the art may make some modifications and improvements without departing from the concept of the present application, which are within the protection scope of the present application.

The invention claimed is:

1. A pipeline endoscope probe, comprising:
    a housing (10), defining an accommodating chamber (11) and a through hole (12) communicated with the accommodating chamber (11);
    an image capturing device (30), wherein the image capturing device (30) is arranged in the accommodating chamber (11) and the image capturing device (30) is oriented towards the through hole (12), the image capturing device (30) comprises a lens (31) and a first control board (32), wherein the lens (31) is configured to capture images, and the first control board (32) is configured to receive the images captured by the lens (31) and converts the images into image signals;
    a lighting device (80), arranged on the housing adjacent to the through hole (12), and a lighting direction of the lighting device (80) matches orientation of the image capturing device (30) to illuminate an environment in front of the image capturing device (30); and
    an eccentric member (20), wherein the eccentric member (20) is rotatably arranged in the accommodating chamber (11), the image capturing device (30) is fixedly connected to the eccentric member (20), and the image capturing device (30) is coaxial with the eccentric member (20) and rotates around an axis of the image capturing device (30) under action of the eccentric member (20), thereby when the pipeline endoscope probe is inserted into a pipeline, and the eccentric member rotates under action of gravity, thereby driving the image capturing device to rotate to allow a perspective of the lens of the image capturing device to be upright;
    wherein the eccentric member (20) defines an installation groove (21) and a connecting block (22), at least a portion of the image capturing device (30) is inserted into the installation groove (21) to make the image capturing device (30) coaxial with the eccentric member (20), and the connecting block (22) is configured to be connected to a connecting piece passing through the image capturing device (30), and an outer surface of the eccentric member housing (41) is provided with a wiring groove (412) for passing through a first electrical connection wire (52).

2. The pipeline endoscope probe according to claim 1, further comprising an eccentric member housing (41), a bearing (42), and a first fixing member (43), wherein the eccentric member housing (41) is arranged in the accommodating chamber (11), the bearing (42) is inserted into the eccentric member housing (41), and the eccentric member (20) is rotatably inserted into a bearing hole (421) of the bearing (42); wherein the first fixing member (43) is connected to one end of the eccentric member housing (41) near the bearing (42), and the first fixing member (43) is configured to fix the bearing (42) inside the eccentric member housing (41); wherein an inner wall of the eccentric member housing (41) is provided with a limit protrusion (411) resisting against the bearing (42) to fix the bearing (42) between the limit protrusion (411) and the first fixing member (43).

3. The pipeline endoscope probe according to claim 2, further comprising a second control board (51), wherein the second control board (51) is arranged in the accommodating chamber (11), and the second control board (51) is electrically connected to the lighting device (80) through a first electrical connection wire (52).

4. The pipeline endoscope probe according to claim 1, wherein the lighting device (80) comprises multiple lamp beads (81), the housing (10) is provided with lamp bead grooves (13) around the through hole (12), and the lamp beads (81) are arranged inside the lamp bead grooves (13); the lighting device (80) further comprises a lampshade (82) connected to the housing (10) and covers the lamp bead groove (13) and the through hole (12).

5. The pipeline endoscope probe according to claim 1, further comprising a second electrical connection wire (53), wherein the eccentric member (20) is provided with a wiring hole (23) on one side thereof near the installation groove (21), and the second electrical connection wire (53) passes through the wiring hole (23) to achieve an electrical connection between the first control board (32) and the second control board (51).

6. The pipeline endoscope probe according to claim 1, further comprising a second fixing member (60), wherein the second fixing member (60) is connected to an inner wall of the accommodating chamber (11) and resists against the second control board (51), so that the second control plate (51) is limited between the first fixing member (43) and the second fixing member (60).

7. The pipeline endoscope probe according to claim 1, further comprising a connecting handle (70), wherein the connecting handle (70) comprises a first connecting end (71) and a second connecting end (72), the first connecting end (71) is connected to one end of the housing (10) away from the image capturing device (30), and the second connecting end (72) is configured to be connected to a guide wire; wherein an outer surface of the first connecting end (71) is provided with an external thread (711), the accommodating chamber (11) is provided with an internal thread (111) at one end away from the image capturing device (30), and the external thread (711) is threaded to the internal thread (111).

8. The pipeline endoscope probe according to claim 7, further comprising a sealing ring (90), and an outer surface of the first connecting end (71) is further provided with a sealing groove (712), the sealing ring (90) is arranged in the sealing groove (712), and when the external thread (711) is threaded to the internal thread (111), the sealing ring (90) resists against between an inner wall of the accommodating chamber (11) and an inner wall of the sealing groove (712).

9. The pipeline endoscope probe according to claim 8, wherein the connecting handle (70) comprises a spring (73) arranged between the first connecting end (71) and the second connecting end (72), and the spring is configured to deform under action of an inner wall of the pipeline.

10. The pipeline endoscope probe according to claim 1, further comprising a main control chip (100) and a plurality of functional modules, wherein the plurality of functional modules comprises a power module (101), a storage module (102), a flash module (103), a switch control module (104), an infrared lighting module (105), an infrared control module (106), and the lens (31).

11. The pipeline endoscope probe according to claim 10, wherein the power module (101) is configured to convert a first power supply voltage to a stabilized second power supply voltage, the second power supply voltage is configured to supply power to the storage module (102), the flash module (103), and the switch control module (104); a power pin (VCC), a clock signal pin (SCL), and a data pin (SDA) of a storage control chip (U3) of the storage module (102) are all electrically connected to the main control chip (100).

12. The pipeline endoscope probe according to claim 10, wherein a sampling pin (CSB), an input pin (MIS0), an output pin (MOS1), and a clock pin (SCK) of a flash control chip (U6) of the flash module (103) are all electrically connected to the main control chip (100).

13. The pipeline endoscope probe according to claim 12, further comprising a third electrical connection wire (54), wherein the second connection end (72) is provided with an electrical connection part (721), and the third electrical connection wire (54) passes through the first connection end (71) and the spring (73) to be electrically connected between the second control board (51) and the electrical connection part (721), wherein the electrical connection part (721) is electrically connected to the guide wire.

14. The pipeline endoscope probe according to claim 10, wherein a signal transmission end (VP) and an image output end (VODEO OUT) of the switch control module (104) are connected to the main control chip (100), and the signal transmission end (VP) and the image output end (VODEO OUT) are grounded through multiple switch branches (1041), each of the switch branches (1041) includes a resistor (1042) and a control switch (1043) connected in series with the resistor (1042).

15. The pipeline endoscope probe according to claim 10, wherein the infrared lighting module (105) includes a transistor (Q2) and a light-emitting element (D6), a control end of the transistor (Q2) is electrically connected to the main control chip (100), a first conductive end of the transistor (Q2) is electrically connected to the power module (101), and a second conductive end of the transistor (Q2) is grounded through the light-emitting element (D6).

16. The pipeline endoscope probe according to claim 10, wherein the infrared control module (106) comprises an infrared filtering control chip (U4), which is an IR-CUT dual filter control chip configured to control operation of infrared dual filter plates in the lens (31).

17. A pipeline endoscope assembly, comprising a display (15) and a pipeline endoscope probe, wherein the pipeline endoscope probe is configured to be in a communication connection with the display (15) and to transmit image signals to the display (15), the pipeline endoscope probe comprises:
a housing (10), defining an accommodating chamber (11) and a through hole (12) communicated with the accommodating chamber (11);
an image capturing device (30), wherein the image capturing device (30) is arranged in the accommodating chamber (11) and the image capturing device (30) is oriented towards the through hole (12), the image capturing device (30) comprises a lens (31) and a first control board (32), wherein the lens (31) is configured to capture images, and the first control board (32) is configured to receive the images captured by the lens (31) and converts the images into image signals; and
a lighting device (80), arranged on the housing (10) adjacent to the through hole (12), and a lighting direction of the lighting device (80) matches orientation of the image capturing device (30) to illuminate an environment in front of the image capturing device (30), wherein a lighting device (80) comprises multiple lamp beads (81) and a transparent lampshade (82), the housing (10) is provided with lamp bead grooves (13) around the through hole (12), and the lamp beads (81) are arranged inside the lamp bead grooves (13), the lampshade (82) is connected to the housing (10) and covers the lamp bead groove (13) and the through hole (12), wherein the lampshade (82) is a planar plate comprising a first flat surface (821), an opposite second flat surface (822) and a central through hole (823) running through the first flat surface (821) and the second flat surface (822), the central through hole (823) surrounds the through hole (12), the first flat surface (821) is inserted in the lamp bead groove (13) and faces the multiple lamp beads (81), and the second flat surface (822) faces outside and is flush with an end of the lamp bead groove (13).

18. The pipeline endoscope assembly according to claim 17, further comprising:
an eccentric member (20), wherein the eccentric member (20) is rotatably arranged in the accommodating chamber (11), the image capturing device (30) is fixedly connected to the eccentric member (20), and the image capturing device (30) is coaxial with the eccentric member (20) and rotates around an axis of the image capturing device (30) under action of the eccentric member (20), thereby when the pipeline endoscope probe is inserted into a pipeline, and the eccentric member rotates under action of gravity, thereby driving the image capturing device to rotate to allow a perspective of the lens of the image capturing device to be upright;
an eccentric member housing (41) and a bearing (42), wherein the eccentric member housing (41) is arranged in the accommodating chamber (11), the bearing (42) is inserted into the eccentric member housing (41), and the eccentric member (20) is rotatably inserted into a bearing hole (421) of the bearing (42), and an outer surface of the eccentric member housing (41) is provided with a wiring groove (412) for passing through an electrical connection wire.

19. The pipeline endoscope assembly according to claim 17, further comprising a connecting handle (70), wherein the connecting handle (70) comprises a first connecting end (71), a second connecting end (72), and a spring (73) arranged between the first connecting end (71) and the second connecting end (72), the first connecting end (71) is connected to one end of the housing (10) away from the image capturing device (30), the second connecting end (72) is away from the housing (10) and is provided with an electrical connection part (721), and the spring (73) is configured to deform under action of an inner wall of the pipeline.

\* \* \* \* \*